United States Patent [19]

Karasawa et al.

[11] Patent Number: 4,547,280
[45] Date of Patent: Oct. 15, 1985

[54] MALTOSE SENSOR

[75] Inventors: Yoshiharu Karasawa, Tokyo; Yoshinori Takata, Chiba, both of Japan

[73] Assignee: Hitachi, Ltd., Tokyo, Japan

[21] Appl. No.: 674,693

[22] Filed: Nov. 26, 1984

[30] Foreign Application Priority Data

Nov. 28, 1983 [JP] Japan .................. 58-222047

[51] Int. Cl.$^4$ .......................... C12Q 1/40; C12Q 1/54
[52] U.S. Cl. .................... 204/403; 204/1 T; 204/415; 204/435; 435/4; 435/14; 435/22; 435/291; 435/817
[58] Field of Search ............... 204/1 E, 403, 415, 435; 435/4, 22, 14, 817, 291

[56] References Cited

U.S. PATENT DOCUMENTS

| 4,169,765 | 10/1979 | Keyes | 435/291 |
| 4,172,765 | 10/1979 | Keyes | 435/14 |
| 4,354,913 | 10/1982 | Pungor et al. | 204/1 T X |

FOREIGN PATENT DOCUMENTS

| 142248 | 6/1980 | German Democratic Rep. | 204/403 |
| 97863 | 8/1981 | Japan | 435/22 |
| 177699 | 11/1982 | Japan | 435/22 |
| 160861 | 9/1983 | Japan | 435/22 |
| 193448 | 11/1983 | Japan | 435/4 |

Primary Examiner—G. L. Kaplan
Attorney, Agent, or Firm—Antonelli, Terry & Wands

[57] ABSTRACT

In a method for assaying maltose to quantitatively determine amylase, which comprises an enzyme membrane having immobilized α-glucosidase and glucose oxidase, the present invention is an improvement of the enzyme electrode for assaying maltose, where a hydrogen peroxide electrode provided with a palladium cathode is used.

3 Claims, 3 Drawing Figures

MALTOSE SENSOR

BACKGROUND OF THE INVENTION

This invention relates to an enzyme electrode for assaying maltose, and particularly to a stable maltose sensor with a long life.

Maltose is a dimer of glucose and is produced when polysaccharides such as starch, etc. are hydrolyzed by α-amylase (which will be hereinafter referred to as "amylase"), etc. Thus, the amount of amylase can be determined indirectly by allowing amylase to act on a system containing an excess and a predetermined amount of a substrate, and measuring the amount of maltose thus produced.

Amylase is an enzyme capable of decomposing polysaccharides such as starch, dextrin, glycogen, pectin, etc. as a substrate into maltose, and exists in organs of animals including human being, plants and microorganisms. Diagnosis of various diseases can be made by quantitative analysis of amylase in biological fluids such as blood, etc., and thus the quantitative determination of amylase has been recently regarded as particularly important.

Heretofore available methods for quantitative analysis of amylase include (1) an amyloclastic method for tracing gradual decomposition of starch by amylase according to iodine-starch reaction, (2) a saccharogenic method for measuring the reducibility of maltose produced through decomposition by amylase, (3) a chromogenic substrate method for colorimetry of soluble pigments freed from insoluble colored starch, as cross-linked with pigments, as a substrate under the action of amylase, etc. Particularly when the sample is a biological fluid, these methods have a drawback of poor assaying accuracy, because various substances contained in the biological fluid, for example, urea, ureic acid, protein, sugars, vitamin C, etc. act as assay-interferring substances, and also have further drawbacks of complicated assaying operation and prolonged assay time.

To overcome these drawbacks, enzymatic methods have been recently developed, which include (4) a maltose phosphorylase method comprising decomposing maltose, which has been produced from soluble starch as a substrate by α-amylase, by maltophosphorylase and ultimately measuring the amount of NADH (reduced nicotinamid adenin dinucleotide) after further three enzyme reaction stages each using β-phosphoglucomutase, glucose-6-phosphate dehydrogenase, and 6-phosphogluconic acid dehydrogenase, (5) an α-glucosidase method comprising decomposing maltose into glucose by α-glucosidase and assaying the glucose, etc. These enzymatic methods utilize the specificity of enzyme for substrates, and thus have such an advantage as no substantial susceptibility to the influence of the assay-interfering substances, as compared with said methods (1) to (3), but have such disadvantages as a prolonged assay time, an impossibility to assay the whole blood, use of expensive analytical reagents such as enzymes and coenzymes, complicated structures of analytical instruments.

To improve the assaying accuracy and simplify the operating procedure, an enzyme sensor method for assaying amylase has been recently proposed [K. Yoda and T. Tsuchida: Proceedings of the International Meeting on Chemical Sensors, page 648 (1983)]. The principle of the method can be outlined by the following enzymatic reactions.

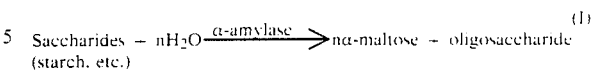

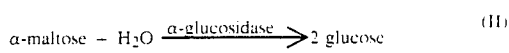

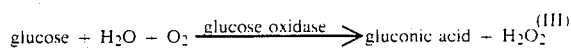

That is, when oxidation reaction of glucose is carried out with glucose oxidase as an enzyme in the case of assaying glucose, oxygen $O_2$ is consumed to produce hydrogen peroxide $H_2O_2$ according to said equation (III). Different from glucose, said oxygen or hydrogen peroxide can be a target of electrochemical measurement, and thus a glucose concentration can be indirectly measured by electrochemically measuring a decrease in the oxygen amount due to its consumption or an amount of hydrogen peroxide thus produced. In assaying maltose, α-maltose produced from the saccharides (substrate) by decomposition under the action of amylase contained in the sample according to said equation (I) reacts with water under the action of enzyme α-glucosidase to produce two molecules of glucose according to said equation (II), and the glucose reacts with water and oxygen under the action of enzyme glucose oxidase to produce gluconic acid and hydrogen peroxide according to said equation (III). In this case, the amount of glucose can be indirectly measured by electrochemically measuring an amount of hydrogen peroxide thus produced, or an amount of oxygen thus decreased in the same manner as described above referring to the assaying of glucose. However, the amount of glucose to be measured in this case is the total amount of the glucose derived from α-maltose produced from the substrate by decomposition by amylase and the glucose existing in the sample from the initial. Amylase can be assayed from a difference of an output signal obtained by assaying maltose corresponding to the total amount of glucose from an output signal corresponding to the initial glucose amount.

An enzyme electrode for the enzyme sensor method comprises an immobilized enzyme membrane in which glucose oxidase and α-glucosidase are immobilized, and a transducer capable of electrochemically measuring a change in chemical reaction, occasioned by catalytic actions of these enzymes. The enzyme sensor method is much better than the conventional methods because of higher assay accuracy, shorter assay time, simple analytical instruments, and no requirements for analytical reagents such as coloring reagents, etc. and thus is a very promising one. However, its effect cannot be fully attained so long as the conventional transducer is used. That is, a galvanic type oxygen electrode, which will be hereinafter referred to as "$O_2$ electrode", and a polarographic type hydrogen peroxide electrode, which will be hereinafter referred to as "$H_2O_2$ electrode", are usually used as the transducer, and the $H_2O_2$ electrode is better as a transducer than the $O_2$ electrode, because the $H_2O_2$ electrode that detects the increasing $H_2O_2$ has a higher signal/noise ratio and a higher stability in the reaction according to said equation (III) than the $O_2$ electrode that detects the decreasing $O_2$. Thus, the $H_2O_2$ electrode is preferable as the transducer.

Generally, a $H_2O_2$ electrode comprises a gold or platinum anode and a silver cathode. A maltose sensor has an enzyme membrane having the immobilized α-glucosidase and glucose oxidase, as described above, on the working surface of said electrode. When the ordinary $H_2O_2$ electrode having a silver cathode is used, it has been found that a very small amount of silver is dissolved out of the cathode to deactivate the immobilized enzymes, particularly β-glucosidase, in the enzyme membrane.

α-Glucosidase is deactivated within a few hours even in the immobilized state, whenever it is placed in an atmosphere containing $Ag^+$ at a concentration of about $10^{-5}$ gram-equivalent/l. On the other hand, the concentration of $Ag^+$ dissolvable from $H_2O_2$ electrode is $10^{-5}$ to $10^{-6}$ gram-equivalent/l at room temperature. Thus, the life of a maltose sensor comprising an $H_2O_2$ electrode provided with a silver cathode is one day as the longest.

SUMMARY OF THE INVENTION

An object of the present invention is to provide a stable maltose sensor with a long life and a high sensitivity.

This and other objects of the present invention can be attained by a maltose sensor comprising an enzyme membrane having immobilized α-glucosidase and glucose oxidase and an electrode, the electrode being a hydrogen peroxide electrode provided with a palladium cathode.

DETAILED DESCRIPTION OF THE PREFERRED EMBODIMENTS

Figure 1:
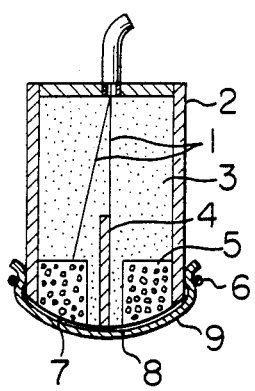
FIG. 1 is a schematic view of a maltose sensor according to one embodiment of the present invention.

The present maltose sensor comprises an enzyme membrane having immobilized α-glucosidase and glucose oxidase and an $H_2O_2$ electrode provided with a palladium cathode.

In the present invention, a $H_2O_2$ electrode provided with a palladium cathode is used for the following reasons:

(1) Palladium has a smaller solubility than silver, and cannot deteriorate the enzyme activity.

(2) Palladium ions less deteriorate the activity of α-glucosidase than silver ions, and the degree of deterioration by palladium ions is about 1/10—about 1/50 times that by silver ions.

(3) Different from other metal species, for example gold, platinum, iridium, osmium, etc., palladium stably works when used as a $H_2O_2$ electrode, though its exact reason has not been clarified yet.

The palladium cathode can take just the same shape as that of the cathode in the Clark type $H_2O_2$ electrode. It is preferable that the palladium has a high purity of at least 99%.

Any membrane having immobilized α-glucosidase and glucose oxidase can be used in the present invention as an enzyme membrane. Well known art as to methods for immobilizing these enzymes and preparing immobilized membranes, for example, the art disclosed in "Immobilized Enzyme" compiled by I. Chibata and published by Kodansha Scientific Publishing Co., Tokyo (1975) can be used in the present invention.

The present invention will be described in detail below, referring to the drawings and Examples.

FIG. 1 is a schematic view of a maltose sensor according to one embodiment of the present invention, where numeral 1 is lead wires, 2 a sensor outside cylinder, 3 an insulator, 4 a platinum anode, and 5 a palladium cathode, and a $H_2O_2$ electrode is constituted from the foregoing members 1 to 5. Numeral 6 is an O-ring for fixing an enzyme membrane 9 to working surface 7 of the $H_2O_2$ electrode through an electrolyte 8. In the enzyme membrane 9, α-glucosidase and glucose oxidase are immobilized. Whenever glucose in a sample contacts the enzyme membrane 9, reaction takes place according to said equation (III). Whenever maltose contacts the enzyme membrane 9, reactions likewise occur according to said equations (II) and (III). $H_2O_2$ formed through these reactions is converted to electric current at the $H_2O_2$ electrode, and the amount of glucose or maltose can be measured.

EXAMPLE 1

Figure 2:
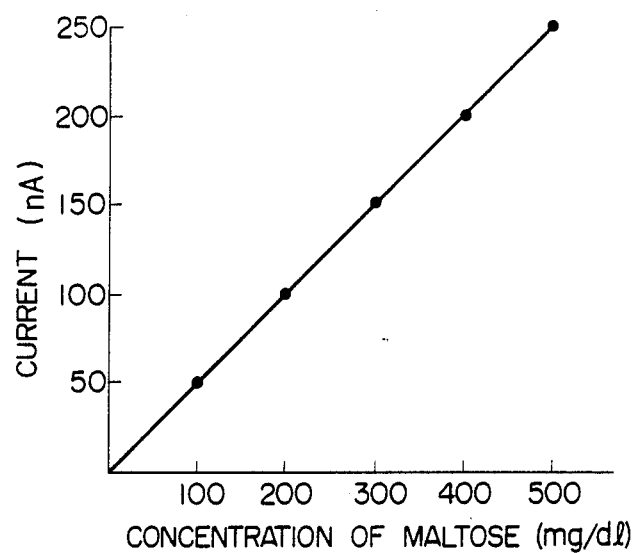
FIG. 2 is a diagram showing a calibration curve of maltose.

20 mg of α-glucosidase (100 mg/U, made by Toyobo Co., Ltd., Japan), 2.5 mg of glucose oxidase (100 mg/U, made by Toyobo Co., Ltd. Japan) and 2 mg of albumin (made by Sigma, Inc., U.S.A.) were dissolved in 400 μl of phosphate buffer solution (pH 6.8, 0.1 mole/l), and the solution was ice-cooled and admixed with 50 μl of 5% glutaraldehyde, followed by immediate stirring. 150 μl of the resulting solution was applied to polyester unwoven cloth having a diameter of 47 mm and a thickness of about 25 μm, and then the cloth was dried in the air for 15 hours, and washed to obtain an enzyme membrane having immobilized α-glucosidase and glucose oxidase. The enzyme membrane was fixed to a $H_2O_2$ electrode (anode diameter: 1.5 mm, cathode outer diameter: 8 mm and inner diameter: 2.5 mm) having the structure as shown in FIG. 1 by means of O-ring to obtain a maltose sensor. Maltose at a concentration of 100 mg/dl was assayed, where 95% response time was 15 seconds. Then, maltose at various concentrations was assayed after dilution to 20-hold individually. Its calibration curve is shown in FIG. 2.

On the other hand, another same maltose sensor as above was made except that silver was used for the cathode, and the durability of these two sensors was compared. The relative response of the maltose sensor provided with the silver cathode was reduced to 0 in a day. Whereas that of the sensor provided with the palladium cathode was maintained at 80% still after 80 days.

EXAMPLE 2

Figure 3:
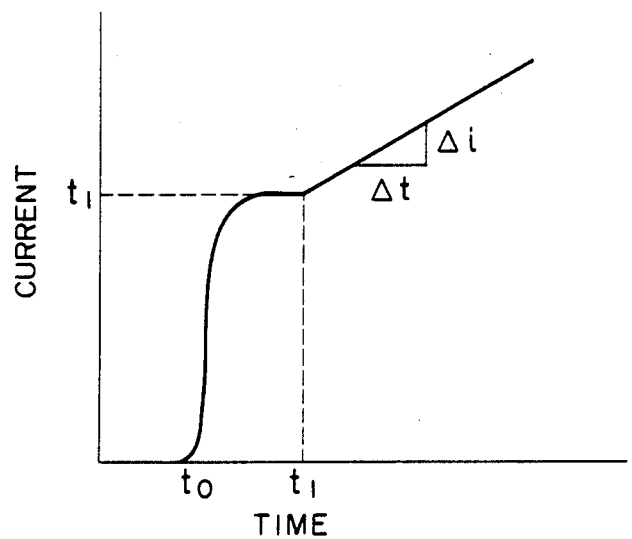
FIG. 3 is a diagram showing the state of output current from a maltose sensor of the present invention when used for assaying amylase.

Amylase was assayed with the maltose sensor provided with the palladium cathode, made in Example 1. That is, the sensor was mounted on an assay cell provided with a stirrer and a thermostat. The assay cell was kept at 37° C., and a phosphate buffer solution at 0.1 mole/l and pH 7.0 was filled therein, and 20 μl of control serum containing amylase and 80 mg/dl of glucose was added thereto as a sample. Then, glucose in the sample was assayed. Then, 20 μl of said phosphate buffer solution containing maltopentaose at a concentration of 0.2 g/l was added thereto as a substrate, and a rate of maltose produced by decomposition by amylase was measured. Relationship with output current from the sensor during the measurement is shown in FIG. 3, where $t_1$ is 15 seconds, $i_1$ 100 nA, and $$\frac{\Delta i}{\Delta t}$$

is 6 nA/min.

When amylase was assayed in the same manner as above 30 days thereafter, $$\frac{\Delta i}{\Delta t}$$

was a little changed, but the change was still in the measurable range at the same time intervals as the initial.

EXAMPLE 3

Serum was assayed in the same manner as in Example 2, and the same sample was also assayed according to blue starch method (a kind of chromogenic substrate method) so far widely used as the conventional method at the same time to compare the results. Correlation coefficient at that time was 0.995 (n=20) and was in a good agreement with that of the conventional method.

As described above, maltose can be assayed accurately and rapidly in the present invention, and the present sensor has a long durability and requires no replacement of the enzyme membrane for a long time, and thus is very economical.

The present sensor can assay amylase particularly in a biological fluid and is very useful in the field of clinical examinations for diagnosis of diseases. Furthermore, the present sensor can assay not only glucose and maltose, but also maltose and glucose-producing substances other than amylase.

What is claimed is:

1. A maltose sensor which comprises an enzyme membrane having immobilized α-glucosidase and glucose oxidase and an electrode, the electrode being a hydrogen peroxide electrode provided with a palladium cathode.

2. A maltose sensor according to claim 1, wherein the palladium cathode is palladium having a purity of at least 99%.

3. A maltose sensor according to claim 1 or 2, wherein the hydrogen peroxide electrode is provided with a platinum anode.

* * * * *